United States Patent [19]

Schaffhausen

[11] Patent Number: 4,906,778

[45] Date of Patent: Mar. 6, 1990

[54] PROCESS FOR THE PRODUCTION OF AMINOGUANIDINE BICARBONATE

[75] Inventor: John G. Schaffhausen, Naperville, Ill.

[73] Assignee: Amoco Corporation, Chicago, Ill.

[21] Appl. No.: 237,993

[22] Filed: Aug. 29, 1988

[51] Int. Cl.$^4$ ............................................. C07C 133/10
[52] U.S. Cl. ..................................................... 564/227
[58] Field of Search ............................................ 564/227

[56] References Cited

U.S. PATENT DOCUMENTS

| | | | |
|---|---|---|---|
| 2,537,328 | 1/1951 | Campbell | 564/227 |
| 3,673,253 | 6/1972 | Simons | 564/227 |

FOREIGN PATENT DOCUMENTS

| | | | |
|---|---|---|---|
| 167251 | 1/1986 | European Pat. Off. | 564/227 |
| 981314 | 12/1982 | U.S.S.R. | 564/227 |
| 885575 | 12/1961 | United Kingdom | 564/227 |

*Primary Examiner*—James H. Reamer
*Attorney, Agent, or Firm*—Matthew R. Hooper; William H. Magidson; Ralph C. Medhurst

[57] ABSTRACT

A process for the preparation of aminoguanidine bicarbonate includes reacting an acidic aqueous hydrazine hydrate solution with calcium cyanamide in an elevated temperature to produce an aminoguanidine solution, recovering the solution, and reacting therewith an alkali metal bicarbonate to produce relatively high purity aminoguanidine bicarbonate.

9 Claims, No Drawings

PROCESS FOR THE PRODUCTION OF AMINOGUANIDINE BICARBONATE

TECHNICAL FIELD

This invention relates to a process for the preparation of aminoguanidine bicarbonate, and in particular to a process wherein the obtained product is relatively pure.

BACKGROUND ART

Aminoguanidine bicarbonate (AGB) is of practical importance because of its use in dyes, dispersants, explosives and other commercial applications.

Processes for the production of AGB may be divided into three groups:
1. Reduction of nitroguanidine or nitrosoguanidine;
2. The hydrazinolysis of nitrosoguanidine or S-alkylisothiourea; and
3. The hydrazination of cyanamide.

The last of these three methods is commercially the most interesting as far as the production of AGB on a large scale is concerned. This process utilizes an aqueous cyanamide, a sodium cyanamide or a calcium cyanamide reacted with hydrazine. The hydrazination process utilizing calcium cyanamide is preferred.

U.S. Pat. No. 3,673,253 to Simons describes a process for producing aminoguanidine bicarbonate in which a calcium cyanamide is reacted with hydrazine in an aqueous medium at a pH of 7 to 9.5. The lowest cyanamide concentration possible must be maintained throughout the reaction as long as the hydrazine concentration is more than about 10 to 30 percent of the initial concentration. This is to prevent formation of dicyandiamide which does not react with hydrazine to produce aminoguanidine in good yields. Sulfuric acid is utilized to adjust the pH. The resulting aminoguanidine solution is treated with a bicarbonate precipitating agent to precipitate the AGB (column 2, lines 4-60). However, the presence of iron contaminants result in this AGB product being yellow in color which is unacceptable, especially if further processing into triazoles, azo dyes, sensitizers and the like is desired. To obtain AGB which is white in color, an additional processing step to remove the iron contaminants from the solution must be performed before addition of the precipitating agent. Alternatively, the iron contaminates are precipitated out with the calcium sulfate thus contaminating the calcium sulfate (column 3, line 53 - column 4, line 44). Each additional step is time-consuming and costly. Also, contamination of the calcium sulfate is undesirable. According to Simons, the reaction of calcium cyanamide with hydrazine in an acid medium having a pH of from 5 to 6 produces unacceptable laboratory yields of only 45 to 65 percent. In large scale batches, the yield is further reduced because the calcium sulfate "sludge" is almost impossible to wash out (column 1, lines 66-73).

An object of the present invention is to provide a process for producing relatively pure AGB in relatively high yields from calcium cyanamide, hydrazine hydrate and a bicarbonate which eliminates specific steps to remove contaminants present in the starting materials and contamination of precipitates of the process by these contaminants.

SUMMARY OF THE INVENTION

In the process of the present invention, calcium cyanamide is added to a hydrazine hydrate solution having an acidic pH. This reaction produces an aminoguanidine solution containing inorganic salts which are filtered off. Thereafter an alkali metal bicarbonate is added to the aminoguanidine solution. The resulting precipitate is aminoguanidine bicarbonate (AGB) which can be recovered as a solid which is relatively pure and white in color. Yields in excess of 90 percent based on hydrazine hydrate are obtained.

A specific step to remove contaminants, especially iron contaminants which discolor the AGB, from the aminoguanidine solution is not necessary. Also, the inorganic salt is not adversely affected by the contaminants.

By maintaining the pH in the acidic range decomposition and polymerization of the calcium cyanamide is prevented. The majority of the contaminants remain in solution.

Advantageously, decomposition of the reagents is avoided and reagents which are stable and readily available are utilized.

Numerous other advantages and features of the present invention will become readily apparent from the following detailed description of the invention, accompanying examples and the appended claims.

DETAILED DESCRIPTION

While this invention is susceptible to embodiment in many different forms, preferred embodiments of the invention are shown. It should be understood, however, that the present disclosure is to be considered as an exemplification of the principles of this invention and is not intended to limit the invention to the embodiments illustrated.

The present process for the preparation of aminoguanidine bicarbonate (AGB) produces high yields and a product which is extremely pure and white in color. The process includes the reaction of calcium cyanamide, hydrazine hydrate, and an alkali metal bicarbonate in an acidic pH solution.

The calcium cyanamide is admixed with an aqueous hydrazine hydrate solution having an acidic pH. Admixing occurs at about ambient temperatures. The temperature of this reaction admixture is then elevated to a temperature adequate to react the calcium cyanamide with the hydrazine hydrate and maintained at this temperature for a time period sufficient to produce an aminoguanidine solution. The aminoguanidine solution is recovered. An alkali metal bicarbonate is added to the recovered solution in an amount sufficient to precipitate AGB which is then recovered.

The calcium cyanamide suitable for use in the present invention is of a commercial grade, although purer grades are also suitable. Thus a large percent of impurities, e.g., carbon oxide, calcium oxide, sulfides, metal salts and the like, can be present. Good yields have been obtained with a crude calcium cyanamide having an assumed purity of about 50 weight percent calcium cyanamide. The calcium cyanamide is preferably ground to a particle size of about 200 mesh, U.S. Sieve Series.

The hydrazine hydrate is present in an aqueous solution containing at least about 40 weight percent hydrazine hydrate. The pH of this solution is acidic, with a preferred pH in a range of about 5 to about 6. The calcium cyanamide will not decompose or polymerize at a temperature below the temperature at which the calcium cyanamide and hydrazine hydrate react if the pH is proper. Also, the hydrazine hydrate is yield determinative.

Suitable alkali metal bicarbonates include the bicarbonates of sodium, potassium, lithium, rubidium, cesium and francium. Sodium bicarbonate and potassium bicarbonate are preferred.

The weight ratio of hydrazine hydrate to calcium cyanamide preferably is in the range of 0.3:1 to about 0.9:1, more preferably about 0.5:1 to about 0.8:1, respectively.

The weight ratio of hydrazine hydrate to the subsequently added alkali metal bicarbonate preferably is in the range of about 0.15:1 to about 1.1:1, more preferably about 0.3:1 to about 0.5:1, respectively.

All weight ratios are based on dry weight of reagents normalized to 100% purity.

In an embodiment of the present process, the pH of an aqueous hydrazine hydrate solution having an ambient temperature in the range of about 5 to about 30° C. is adjusted to an acidic pH. For a given temperature of the solution, the pH is adjusted to a value which inhibits decomposition and/or polymerization of the calcium cyanamide which is added. For example, when the temperature of the solution is about 10° C., the pH is adjusted to a range of about 5 to about 6 by the dropwise addition of a suitable acid, e.g., concentrated sulfuric acid, while providing agitation. This is the initial pH for the reaction admixture.

Powdered calcium cyanamide is slowly admixed with the hydrazine hydrate solution while maintaining agitation to produce a reaction admixture. During addition of the calcium cyanamide the pH is maintained at about the initial pH by the addition of the suitable acid.

The temperature of the reaction admixture is then raised to a temperature in the range of about 75 to about 95° C. During this temperature increase the pH is maintained at about the initial pH. The reaction admixture is maintained at this temperature for a time period of about 1 to 4 and preferably about 2 hours. During this time period the pH is maintained at about the initial pH.

At the end of this time period the reaction admixture is filtered to remove calcium salts that have precipitated out. The filtrate is an aminoguanidine solution. The filtrate is admixed with water and utilized to wash the resultant filter cake well. The filtrate and the wash water are combined and the obtained admixture is cooled to a temperature in a range of about 0 to about 10° C.

An alkali metal bicarbonate is added thereto under agitation. Precipitation of AGB begins in a short time. The precipitated AGB is recovered, usually by filtration, and dried. The recovered AGB is of relatively high purity, i.e., 90% or higher.

The AGB produced by the method of the present invention is white in color despite iron contaminants that are present in the calcium cyanamide. By cooling the filtrate and water admixture to a temperature of about 0 to about 10° C. and adjusting the pH to the acid range before precipitating out AGB, the iron contaminants remain in solution.

The following example describes the process of the present invention, but is not to be construed as a limitation thereon.

EXAMPLE 1

An aqueous solution of hydrazine hydrate, in 500 ml of water (25 grams of Practical Grade; 62 wt%) was cooled in an ice-salt bath to a temperature of about 10° C. The pH of the solution was adjusted to about 5 to about 6 by the dropwise addition of concentrated sulfuric acid.

Powdered calcium cyanamide (50 grams, Alpha No. 29462 ground to a particle size of approximately 200 mesh, U.S. Sieve Series) was added over a time period of about 5 minutes. The exotherm of about 4° C. was observed. The weight ratio of hydrazine hydrate to calcium cyanamide was about 0.6:1.

The bath was removed and the temperature of the resulting reaction mixture was raised to about 25° C. The pH was again adjusted to a value within the range of about 5 to about 6 with concentrated sulfuric acid.

Subsequently, the temperature of the reaction mixture was raised to about 85° C. and the mixture held at this temperature for a time period of about 2 hours. The pH value was maintained in the range of about 5 to about 6 during the reaction, by addition of sulfuric acid as necessary.

At the end of this time period, precipitated calcium salts were filtered off and washed well with a wash solution of the filtrate combined with water. The wash solution was cooled in an ice bath to a temperature in the range of about 0 to about 10° C.

Sodium bicarbonate (39.1 grams) was then added under agitation. Precipitation of the AGB began after several minutes and continued for 2 hours. The AGB was filtered off and dried. The yield obtained was 39 grams (92.4% based on hydrazine hydrate) as a white solid.

This invention has been described in details of specific embodiments set forth in detail, but it should be understood that these are by way of illustration only and that the invention is not necessarily limited thereto. Modifications and variations will be apparent from this disclosure and may be resorted to without departing from the spirit of this invention, as those skilled in the art will readily understand. Accordingly, such variations and modifications of the disclosed products are considered to be within the purview and scope of this invention and the following claims.

I claim:

1. A method of preparing aminoguanidine bicarbonate which comprises
    combining calcium cyanamide with hydrazine hydrate in an aqueous solution at a pH of about 5 to 6 and at about ambient temperature to produce a reaction mixture;
    elevating the temperature of the reaction admixture so as to react calcium cyanamide with hydrazine hydrate to produce an aminoguanidine solution while maintaining said pH range;
    recovering the aminoguanidine solution;
    adding to the recovered aminoguanidine solution an alkali metal bicarbonate in an amount sufficient to precipitate aminoguanidine bicarbonate; and
    recovering the precipitated aminoguanidine bicarbonate.

2. A method of preparing aminoguanidine bicarbonate in accordance with claim 1 wherein calcium cyanamide and hydrazine hydrate are combined at a temperature in the range of about 5 to about 30° C.

3. A method of preparing aminoguanidine bicarbonate in accordance with claim 1 wherein the reaction is carried out at an elevated temperature in the range of about 75 to about 95° C.

4. A method of preparing aminoguanidine bicarbonate in accordance with claim 1 wherein the aqueous solution of hydrazine hydrate contains at least about 40 weight percent hydrazine hydrate.

5. A method of preparing aminoguanidine bicarbonate in accordance with claim 1 wherein the alkali metal bicarbonate is selected from the group consisting of sodium bicarbonate and potassium bicarbonate.

6. A method of preparing aminoguanidine bicarbonate in accordance with claim 1 wherein the weight ratio of hydrazine hydrate to calcium cyanamide is in the range of about 0.3:1 to about 0.9:1.

7. A method of preparing aminoguanidine bicarbonate in accordance with claim 1 wherein the weight ratio of hydrazine hydrate to alkali metal bicarbonate is in the range of about 0.15:1 to about 1.1:1.

8. Aminoguanidine bicarbonate of relatively high purity produced in accordance with the method of claim 1.

9. A method of preparing aminoguanidine bicarbonate which comprises:

combining calcium cyanamide with hydrazine hydrate in a weight ratio in the range of about 0.3:1 to about 0.9:1 in an aqueous solution at a pH in the range of about 5 to about 6 and a temperature of about 10° C. to produce a reaction admixture;

elevating the temperature of the reaction admixture to a value of about 75 to about 95° C. to react calcium cyanamide with hydrazine hydrate to produce an aminoguanidine solution and maintaining said pH range during the reaction;

recovering the aminoguanidine solution;

adding to the recovered aminoguanidine solution an alkali metal bicarbonate present in a weight ratio of hydrazine hydrate to alkali metal bicarbonate in the range of about 0.15:1 to about 1.1:1, to precipitate aminoguanidine bicarbonate; and recovering the precipitated aminoguanidine bicarbonate.

* * * * *